United States Patent
Murugesan et al.

(10) Patent No.: US 10,629,291 B2
(45) Date of Patent: Apr. 21, 2020

(54) ANTIBIOTIC RESISTANCE CAUSATION IDENTIFICATION

(71) Applicant: KONINKLIJKE PHILIPS N.V., Eindhoven (NL)

(72) Inventors: Karthikeyan Murugesan, Cambridge, MA (US); Nevenka Dimitrova, Pelham Manor, NY (US); Henry Lin, Quincy, MA (US); Pramod Mayigowda, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/454,548

(22) Filed: Mar. 9, 2017

(65) Prior Publication Data

US 2017/0270244 A1    Sep. 21, 2017

Related U.S. Application Data

(60) Provisional application No. 62/418,532, filed on Nov. 7, 2016, provisional application No. 62/306,283, filed on Mar. 10, 2016.

(51) Int. Cl.
*G16B 30/00* (2019.01)
*G16B 20/00* (2019.01)
*G16B 45/00* (2019.01)
*C12Q 1/689* (2018.01)

(52) U.S. Cl.
CPC ............ *G16B 30/00* (2019.02); *C12Q 1/689* (2013.01); *G16B 20/00* (2019.02); *G16B 45/00* (2019.02); *C12Q 2537/165* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2013/0157876 A1 | 6/2013 | Lynch et al. |
| 2014/0030712 A1 | 1/2014 | Zechiedrich et al. |
| 2015/0331993 A1 | 11/2015 | Godbold et al. |

FOREIGN PATENT DOCUMENTS

| WO | 2015007487 A1 | 1/2015 |
| WO | 2015184017 A1 | 12/2015 |

OTHER PUBLICATIONS

Steinig et al. Single-molecule sequencing reveals the molecular basis of multidrug-resistance in ST772 methicillin-resistanct *Staphylococcus aureus*. BMC Genomics 2015, 16:388, p. 1-10.*

(Continued)

*Primary Examiner* — Olivia M. Wise
(74) *Attorney, Agent, or Firm* — Mark Beloborodov

(57) ABSTRACT

Methods and systems for identifying causal genetic mechanisms of antibiotic resistance in pathogens. In accordance with at least one embodiment, the system includes a gene resistance module to identify genes present in an antibiotic resistant pathogen, a single nucleotide polymorphism module to identify mutations present in an antibiotic resistant pathogen, and an antibiotic resistance module configured to output the causation of antibiotic resistance based on the identified genes and mutations.

1 Claim, 13 Drawing Sheets

(56) References Cited

OTHER PUBLICATIONS

Gersting. Section 4.5: Matrices, Ch. 4: Relations, Functions, and Matrices. Mathematical structures for computer science. Macmillan, pp. 321-338 (Year: 2007).*

Rowe, et al., "Search Engine for Antimicrobial Resistance: A Cloud Compatible Pipeline and Web Interface for Rapidly Detecting Antimicrobial Resistance Genes Directly from Sequence Data", PLOS Research Engine for Antimicrobial Resistance, Jul. 21, 2015, pp. 1-12.

Berrazeg, et al., "Hierarchical clustering as a rapid tool for surveillance of emerging antibiotic-resistance phenotypes in Klebsiella pneumoniae strains" Journal of Medical Microbiology (2013), 62, pp. 864-874.

Steiner, et al., "KvarQ: targeted and direct variant calling from fastq reads of bacterial genomes", BMC Genomics 2014, http://www.biomedcentral.com/1471-2164/15/881, pp. 1-12.

Gupta, et al., "ARG-ANNOT, a New Bionformatic Tool to Discover Antibiotic Resistance Genes in Bacterial Genomes", Antimicrobial Agents and Chemotherapy, Jan. 2014, vol. 58, No. 1, pp. 212-220.

Muroi et al., "Application of Matrix-Assisted Laser Desorption Ionization-Time of Flight Mass Spectrometry for Discrimination of Laboratory-Derived Antibiotic-Resistant Bacteria", Biological & Pharmaceutical Bulletin, vol. 35, No. 10, Oct. 2012 (Oct. 2012), pp. 1841-1845.

Daniela et al., "Classification of antimicrobial resistance using artificial neural networks and the relationship of 38 genes associated with the virulence of *Escherichia coli* isolates from broilers", Pesquisa Veterinaria Brasileira, vol. 35, No. 2, Feb. 2015, pp. 137-140.

\* cited by examiner

|  | $S_1$ | $S_2$ | $S_k$ | $S_{k+1}$ | $S_n$ |
|---|---|---|---|---|---|
| $Ref\_Gene_1$ | 1 | 1 | 0 | 0 | 0 |
| $Ref\_Gene_2$ | 0 | 1 | 0 | 0 | 0 |
| $Ref\_Gene_3$ | 0 | 1 | 0 | 0 | 0 |
| $Ref\_Gene_4$ | 1 | 1 | 0 | 1 | 0 |
| $S_1\_Gene_1$ | 1 | 1 | 1 | 0 | 0 |
| $S_1\_Gene_2$ | 1 | 1 | 0 | 1 | 1 |
| $S_1\_Gene_3$ | 1 | 1 | 0 | 0 | 0 |
| $S_2\_Gene_1$ | 1 | 1 | 0 | 1 | 0 |
| . | 0 | 0 | 0 | 0 | 0 |
| . | 0 | 0 | 0 | 0 | 0 |
| . | 0 | 1 | 0 | 1 | 0 |
| $S_j\_Gene_k$ | 1 | 1 | 1 | 1 | 0 |
| . | 0 | 0 | 1 | 1 | 1 |
| . | 0 | 0 | 0 | 0 | 1 |
| . | 0 | 0 | 0 | 0 | 0 |
| . | 1 | 1 | 0 | 0 | 0 |
| $S_n\_Gene_k$ | 0 | 0 | 0 | 1 | 1 |

|  | Gene$_1$ | Gene$_2$ | Gene$_3$ | ... | Gene$_k$ | .. | Gene$_m$ | Labels |
|---|---|---|---|---|---|---|---|---|
| S$_1$ | 0 | 0 | 0 |  |  |  |  | LabelA |
| S$_2$ | 0 |  | ... |  | 1 |  |  | LabelB |
| . |  | 1 | 1 | ... | 1 |  |  | LabelB |
| . |  | 1 |  | 1 |  | 0 |  | LabelA |
| . |  | 1 |  | 0 | ... |  |  | LabelA |
| S$_i$ | 0 |  | 1 |  |  | ... |  | ... |
| . |  |  |  |  |  |  |  | ... |
| . |  |  |  |  |  |  |  | LabelA |
| S$_n$ |  | 1 |  | 0 |  |  |  | LabelB |

|  | Pos | Ref | $S_1$ | $S_2$ | $S_3$ | $S_4$ | ... | $S_i$ | $S_{i+1}$ | ... | $S_n$ |
|---|---|---|---|---|---|---|---|---|---|---|---|
| $SNP_1$ | 3509 | T | T | T | T | T | ... | T | T | ... | N |
| $SNP_2$ | 5105 | A | G | G | G | A | ... | A | G | ... | G |
| $SNP_3$ | 8827 | C | C | C | C | C | ... | C | C | ... | C |
| . | ... | ... | ... | ... | ... | ... | ... | ... | ... | ... | ... |
| $SNP_k$ | 24057 | T | T | T | T | T | ... | T | T | ... | T |
| $SNP_{k+1}$ | 28411 | G | G | G | G | G | ... | G | G | ... | G |
| ... | ... | ... | ... | ... | ... | ... | ... | ... | ... | ... | ... |
| $SNP_m$ | 65684 | C | C | G | C | C | ... | C | C | ... | C |

1002 = , 1004 = Ref, 1008 , 1006 = samples

|  | Pos | Ref | $S_1$ | $S_2$ | $S_3$ | S. | $S_i$ | $S_{i+1}$ | $S_n$ | Label |
|---|---|---|---|---|---|---|---|---|---|---|
| $SNP_1$ | 3509 | T | T | T | T | T | T | T | N | Resistant |
| $SNP_2$ | 5105 | A | G | G | G | A | A | G | G | Sensitive |
| $SNP_3$ | 8827 | C | C | C | C | C | C | C | C | Resistant |
| $SNP_4$ | ... | T | T | T | T | T | T | T | T | Sensitive |
| $SNP_5$ | ... | G | G | G | G | G | G | G | T | Resistant |
| $SNP_k$ | ... | G | G | G | G | G | C | G | G | Sensitive |
| $SNP_{k+1}$ | ... | T | T | T | T | T | T | T | G | Resistant |
| ... | ... | A | A | A | A | A | G | G | C | Resistant |
| $SNP_m$ | 65684 | C | C | C | G | C | C | C | C | Sensitive |

1102 = Label

FIG. 11

| | Gene₁ | Gene₃ | Geneₘ | SNP₂ | ... | SNPₘ | Labels |
|---|---|---|---|---|---|---|---|
| S₁ | 0 | 0 | | | | | LabelA |
| S₂ | 0 | ... | 1 | | | | LabelB |
| . | | 1 | 0 | | | | LabelB |
| . | | 1 | 1 | 0 | | 1 | LabelA |
| . | | 0 | | 0 | | 1 | LabelA |
| Sᵢ | | | | 1 | | 1 | ... |
| . | | | | | | 1 | ... |
| . | | | | | | | LabelA |
| Sₙ | 1 | 0 | 1 | | 1 | | LabelB |

1400

ANTIBIOTIC RESISTANCE CAUSATION IDENTIFICATION

CROSS REFERENCE TO RELATED APPLICATIONS

The present application claims priority to both U.S. Provisional Application Ser. No. 62/418,532, filed Nov. 7, 2016 and U.S. Provisional Application Ser. No. 62/306,283, filed Mar. 10, 2016. These applications are incorporated herein by reference, for all purposes.

TECHNICAL FIELD

Various embodiments described herein relate to methods and systems for identifying causal genetic mechanisms of antibiotic resistance in pathogens and, more particularly but not exclusively, to methods and systems for identifying causal genetic mechanisms of antibiotic resistance.

BACKGROUND

Antibiotic resistance of a microorganism refers to the microorganism's ability to resist the effect of antimicrobial drugs that were developed to treat infections caused by microorganisms. The development of antibiotic resistance in microorganisms is an inevitable biological process. However, antibiotics must be used conservatively, accurately, and not excessively. Antibiotic usage that does not conform with these principles may accelerate the acquirement of resistance in pathogens.

The ESKAPE pathogens in particular, i.e., *Enterococcus faecium Staphylococcus aureus, Klebsiella pneumoniae, Acinetobacter baumanii, Pseudomonas aeruginosa*, and *Enterobacter* species, are known to be major causes of Hospital Acquired Infections in the U.S. One major concerns is the growing antibiotic resistance of the ESKAPE pathogens.

Drug resistance mechanisms that emerge and spread globally challenge medical personnel's ability to treat common bacterial infections by reducing the effectiveness of or completely nullifying the effects of existing treatment methodologies. This inevitably leads to increased healthcare expenditure, increased length of stay at healthcare institution, and eventually leads to a higher mortality rate.

In the U.S. alone, for example, more than 2,000,000 illnesses and at least 23,000 deaths per year are attributed to antibiotic resistance developed in pathogens. These numbers increase globally, with antibiotic resistance causing over 700,000 deaths per year worldwide. If the current trend continues, the number of deaths attributed to antibiotic resistance could reach 10 million with a projected GDP loss of over 100 trillion dollars by 2050.

Antibiotic resistance not only makes diagnosing existing bacterial infections difficult but it also has subsequent effects in other realms of healthcare. For example, antibiotic resistance affects surgeries, organ transplants, caesarean sections, cancer treatment, and other medical conditions and treatments.

Existing techniques for combatting antibiotic resistance generally involve preventing the spread of antibiotic resistant organisms including strategies for controlling antibiotics consumption at the policy and management level, rather than identifying the root cause of the resistance and/or stopping its emergence.

Another strategy is to quantify a pathogen's antibiotic resistance by calculating the isolate's minimum inhibitory concentration for various antibiotics and impeding the spread of resistance by various sanitary approaches in the hospitals. Again, however, these techniques are generally only concerned with containing the dissemination of antibiotic resistant pathogens

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

According to the foregoing, it would be desirable to provide methods and systems that characterize the very cause of resistance acquisition and molecular evolution to help combat antibiotic resistance.

In one aspect, various embodiments relate to a system for identifying antibiotic resistance in pathogens. The system includes a gene-resistance module configured to receive as input a plurality of genome sequences, each sequence comprising a plurality of genes, generate a gene presence-absence matrix that identifies the genes present in each of the plurality of genome sequences, and output a label of resistant or sensitive for each of the plurality of genome sequences; a single nucleotide polymorphism-resistance module configured to receive as input the plurality of genome sequences, identify gene mutations in each of the plurality of genome sequences, and output a label of resistant or sensitive to each identified mutation; and an antibiotic resistance module configured to receive as input the genes and mutations associated with the labels of resistant or sensitive for each of the plurality of genome sequences and each identified mutation, and identify at least one of a gene that confers antibiotic resistance and the source of a gene that confers antibiotic resistance based on the received labels.

In one embodiment, the gene-resistance module further includes a gene prediction engine configured to identify a set of genes present in a sample of the plurality of genome sequences; and a gene elimination engine configured to remove the identified set of genes from each of the plurality of genome sequences, wherein the gene prediction engine and the gene elimination engine are further configured to iterate the steps of identifying a set of genes present in each of the remaining genome sequences and removing the identified sets of genes from the remaining genome sequences to generate the gene presence-absence matrix.

In one embodiment, the gene-resistance module is further configured to generate a value representing a gene's contribution to antibiotic resistance or antibiotic sensitivity.

In one embodiment, the antibiotic resistance module is further configured to determine whether at least two resistant genes operate as a network.

In one embodiment, a gene's presence may be defined by a binary value or a percentage.

In one embodiment, the antibiotic resistance module is further configured to determine whether at least two genes that operate as an operon network include a mutation.

In one embodiment, the antibiotic resistance module is further configured to output a report identifying the at least one gene or mutation that is associated with antibiotic resistance.

In one embodiment, the source of the gene is identified using at least one of sequence composition and phylogeny to classify the genome sequence as host or foreign.

In another aspect, various embodiments relate to a method for identifying antibiotic resistance in pathogens. The method includes receiving, at a gene-resistance module and a single nucleotide polymorphism-resistance module, a plurality of genome sequences, each sequence comprising a plurality of genes; generating, via the gene-resistance module, a gene presence-absence matrix that identifies the genes present in each of the plurality of genome sequences; outputting, via the gene-resistance module, a label of resistant or sensitive for each of the plurality of genome sequences; identifying, via the single nucleotide polymorphism-resistance module, gene mutations in each of the plurality of genome sequences, outputting, via the single nucleotide polymorphism-resistance module, a label of resistant or sensitive to each identified mutation; receiving, at an antibiotic resistance module, the genes and mutations associated with the labels of resistant or sensitive for each of the plurality of genome sequences and each detected mutation; and identifying, via the antibiotic resistance module, at least one of a gene that confers antibiotic resistance and the source of a gene that confers antibiotic resistance based on the received labels.

In one embodiment, the method further includes identifying, via the gene-resistance module, a set of genes present in a sample of the plurality of genome sequences; removing, via the gene-resistance module, the identified set of genes from each of the plurality of genome sequences; and iterating the steps of identifying a set of genes present in each of the remaining samples from the plurality of genome sequences and removing the identified sets of genes from the remaining genome sequences to generate the gene presence-absence matrix.

In one embodiment, the method further includes generating, via the gene-resistance module, a value representing a gene's contribution to antibiotic resistance or antibiotic sensitivity.

In one embodiment, the method further includes determining, via the antibiotic resistance module, whether at least two resistant genes operate as a network.

In one embodiment, a gene's presence may be defined by a binary value or a percentage.

In one embodiment, the method further includes determining, via the antibiotic resistance module, whether at least two genes that operate as a network include a mutation.

In one embodiment, the method further includes outputting, via the antibiotic resistance module, a report identifying at least one gene or mutation that is associated with antibiotic resistance.

In one embodiment, the source of the gene is identified using at least one of sequence composition and phylogeny to classify the genome sequence as host or foreign.

In yet another aspect, various embodiments relate to a method for identifying one or more genes that confer antibiotic resistance. The method includes receiving a plurality of genome sequences, each sequence comprising a plurality of genes; determining which of the plurality of genome sequences confer antibiotic resistance; determining which mutations in the plurality of genome sequences confer antibiotic resistance; and identifying at least one gene in the plurality of genome sequences that is associated with antibiotic resistance based on which samples and mutations confer antibiotic resistance.

BRIEF DESCRIPTION OF THE DRAWINGS

In order to better understand various example embodiments, reference is made to the accompanying drawings, wherein:

FIG. 6 depicts a gene presence-absence matrix in accordance with one embodiment;

FIG. 7 depicts a gene presence-absence matrix in accordance with another embodiment;

FIG. 10 depicts a variant matrix in accordance with one embodiment;

FIG. 11 depicts a variant matrix with resistant-sensitive labels in accordance with one embodiment;

DETAILED DESCRIPTION

Figure 1:
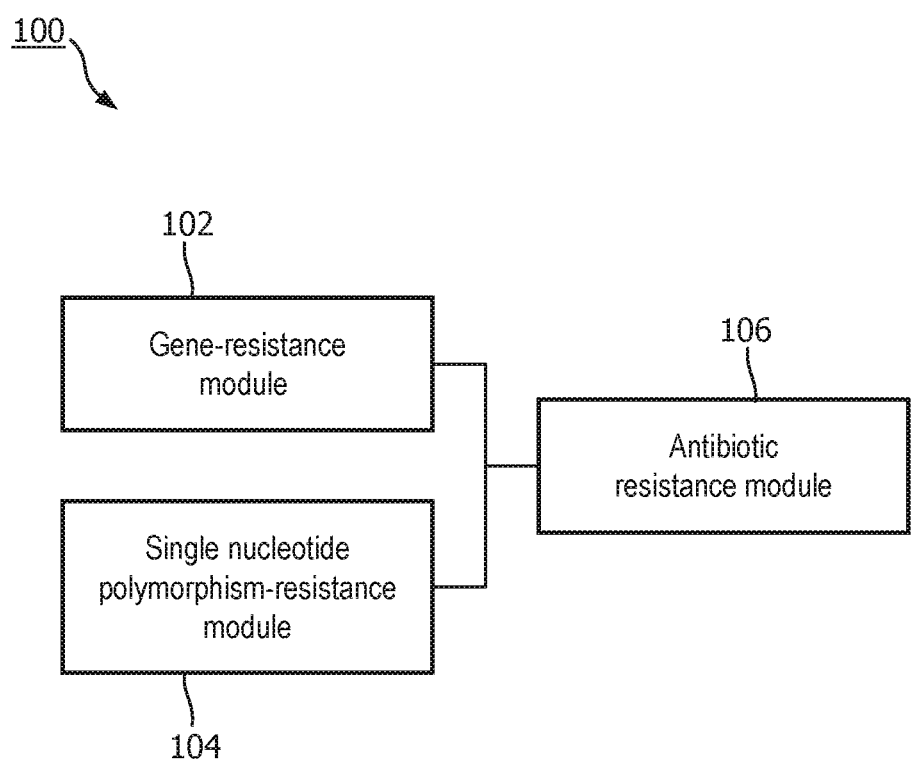
FIG. 1 illustrates a system for identifying antibiotic resistance in pathogens in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

The methods and systems described herein may involve Next Generation Sequencing (NGS) of pathogens to identify mutations, genes, and resistance cassettes associated with antibiotic resistance. FIG. 1 illustrates a system 100 for identifying antibiotic resistance in pathogens in accordance with one embodiment. The system may include a gene-resistance module 102, a single nucleotide polymorphism-resistance (SAR) module 104, and an antibiotic resistance module 106.

The gene-resistance module 102 may identify genes in a pathogen that are responsible for conferring resistance to antibiotics. The SAR module 104 may identify non-synonymous mutations in a pathogen that are responsible for conferring resistance to antibiotics. The outputs of the gene resistance module 102 and the SAR module 104 may be provided to the antibiotic resistance module 106. The antibiotic resistance module 106 may consolidate the information regarding potential biomarkers identified from the SAR and GAR modules and may output a list of SNPs and genes that are associated with antibiotic resistance and the sensitivity and specificity values. The antibiotic resistance module 106 may also output these findings in a report for medical personnel or the like.

Figure 2:
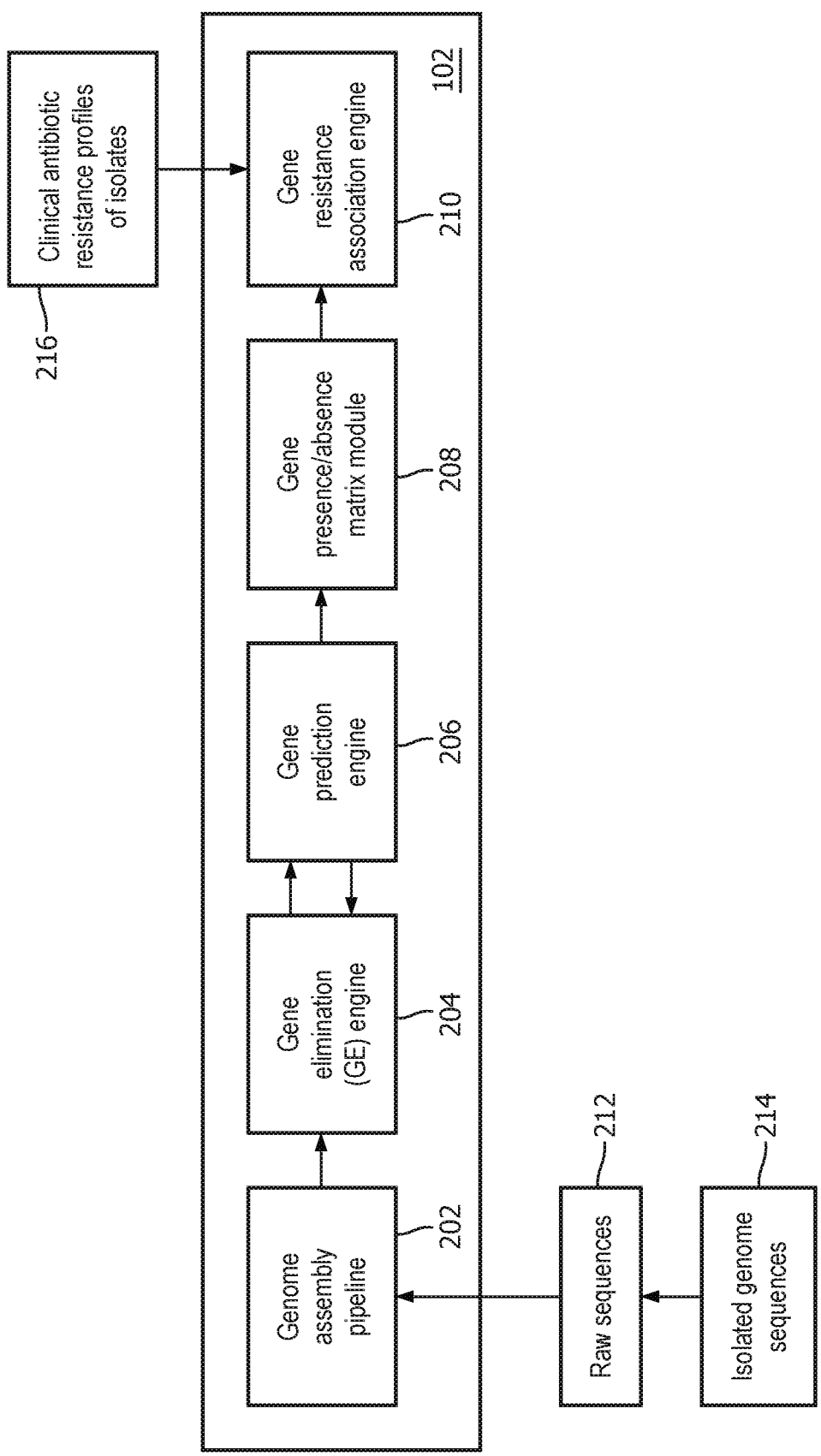
FIG. 2 illustrates the gene resistance module 102 of FIG. 1 in accordance with one embodiment.

FIG. 2 illustrates one embodiment of the gene-resistance module 102 in more detail. As shown, the gene-resistance module 102 may include a genome assembly pipeline 202, a gene elimination engine 204, a gene prediction engine 206, a gene presence/absence matrix module 208, and a gene-resistance association engine 210.

In operation, pathogenic isolates may be extracted from patients in healthcare institutions using any suitable sequencing technique or machine (HiSeq, MiSeq, etc.). The extracted isolates may then be cultured using any appropriate growth media such as chemically defined, complex, reducing, differential, and enrichment-based growth media. The growth media used may vary and may depend on the application.

Next, DNA may be extracted from the cultured isolates using standard laboratory procedures. The extracted DNA may then be prepped for sequencing using any suitable sequencing technique or technology. This process can either be whole genome sequencing or targeted sequencing of the pathogen's genome.

The raw sequences 212 of the isolated genome sequences 214 may then be fed into the genome assembly pipeline module 202 to be deNovo assembled. The genome assembly pipeline module 202 may use assemblers such as SPADES, MASURCA, or any other appropriate genome assembler whether available now or invented hereafter.

The assembled gene sequences may then be fed into the gene elimination engine 204. The gene elimination engine 204 and the gene prediction engine 206 may work in tandem to extract the residual genome devoid of the reference genes from each pathogenic isolate genome sequenced.

Consider a plurality of genome sequences that include a reference genome. The purpose of the gene elimination engine 204 and the gene prediction engine 206 is to identify the presence and/or absence of genes from the cohort of genomes (including a known reference genome) and eliminate the genes present in each of the cohort sequences from the remaining sequences.

Figure 3:
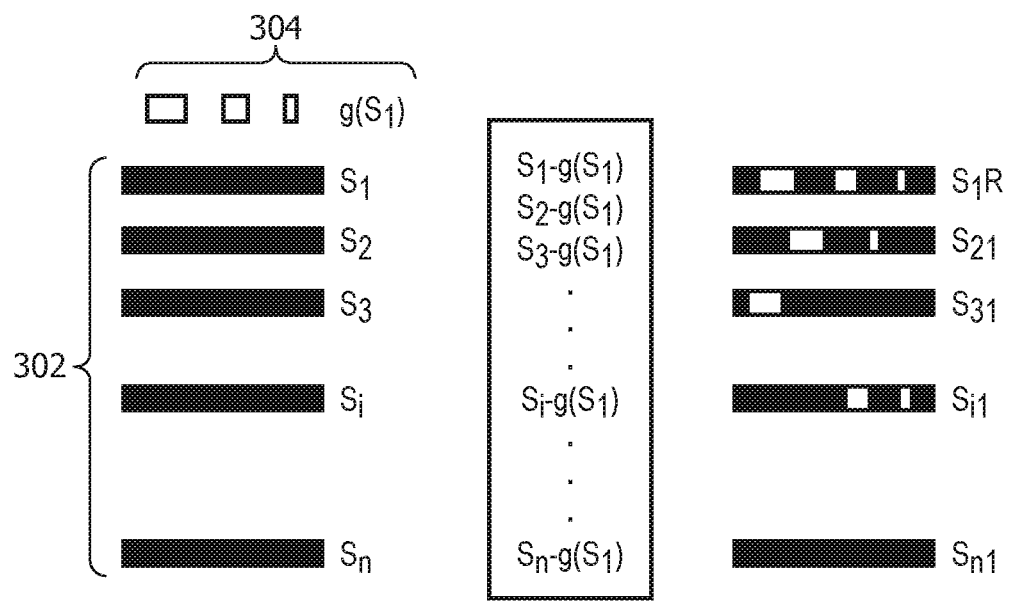
FIG. 3 illustrates a gene prediction and elimination algorithm in accordance with one embodiment.

The deNovo gene elimination algorithm is illustrated in FIG. 3. In FIG. 3, $S_1$ may be considered a reference genome sequence, and $g(S_1)$ 304 may refer to the genes that are predicted in $S_1$. Some of the genes predicted $g(S_1)$ may be present in the other genome sequences (302). The gene elimination engine 204 may then remove $g(S_1)$ from each genome sequence to yield SIR (the remnant residual genome of sequence $S_1$ that is devoid of any predicted genes), $S_{21}$ (the residual genome of $S_2$ after removing all of $S_1$'s deNovo genes from $S_2$), and so on.

Figure 4:
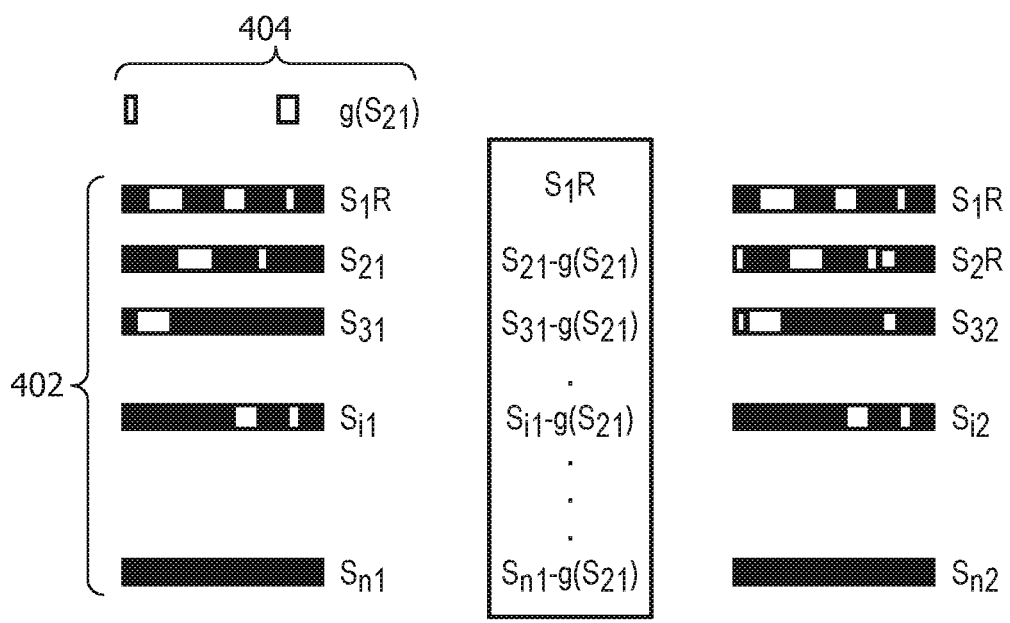
FIG. 4 illustrates a gene prediction and elimination algorithm in accordance with another embodiment.

This is an iterative process that proceeds to the next sample $S_{21}$. The second iteration is illustrated in FIG. 4. FIG. 4 illustrates the remnant residual genome $S_1R$ along with the other residual genomes $S_{21}, S_{31}, S_{i1} \ldots S_{n1}$ (402). $g(S_{21})$ 404 may refer to the genes that are predicted in $S_{21}$. Some of the genes predicted in $S_{21}$ may be present in the other genome sequences. The gene elimination engine 204 may then remove $g(S_{21})$ from each remaining genome sequence $S_{21}$, $S_{31} \ldots S_{i1}, \ldots S_{n1}$. This yields $S_1R$, $S_2R$ (the remnant residual genome of sequence $S_2$ that is devoid of any genes), $S_{32}, \ldots S_{i2}, \ldots S_{n2}$, and so on. This provides a computationally fast and cheap method to gather data regarding the genes present in each sequence.

Figure 5:
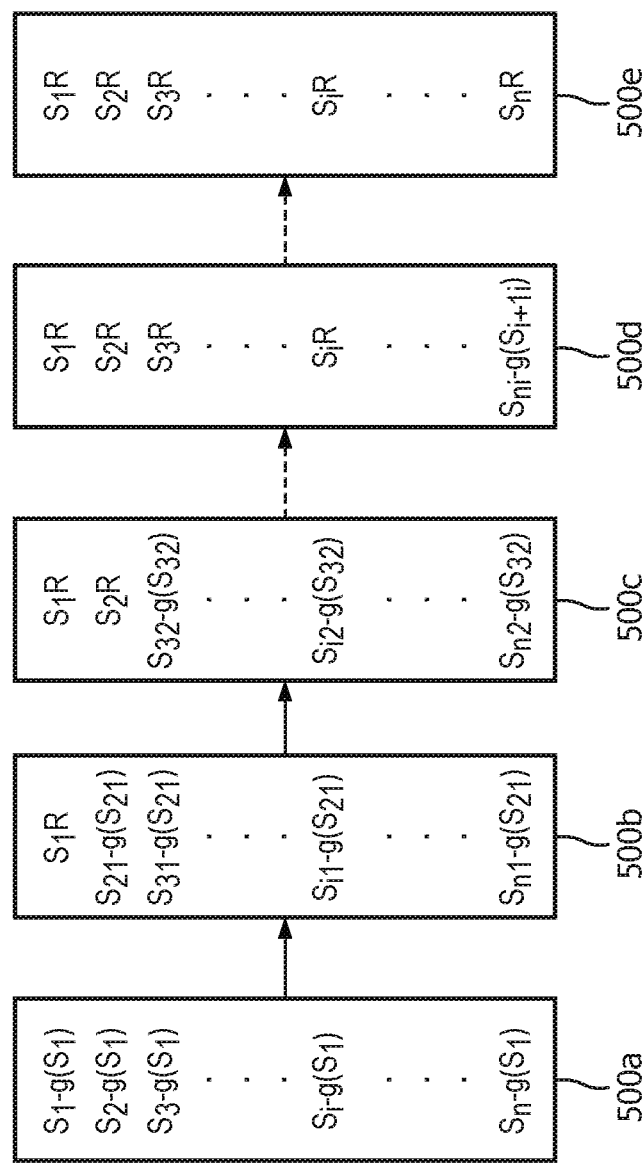
FIG. 5 illustrates multiple iterations of a gene prediction and elimination algorithm in accordance with one embodiment.

This iterative process may be performed for each genome sequence until the residual genome of all input samples has been generated. FIG. 5, for example, shows multiple iterations 500a-e of the algorithms shown in FIGS. 3 and 4. Additionally, the pseudocode for this procedure is depicted below:

```
i=1
    while (i<n)       //(S1,S2...Si......Sn) -> (S1R,S2R,...SiR....SnR)
    {
        g(Si(i-1)) = gene_prediction(Si(i-1))
        gene_elimination(g(Si(i-1))
        {
            SiR<-Si(i-1)-g(Si(i-1))
            for(k=i+1;k<=n;k++)
            {
                Ski<-Sk(i-1)-g(Si(i-1))
            }
        i++
    Update gene_PA_mat [ ]
        }
```

As the gene elimination engine 204 and the gene prediction engine 206 repeat these iterations, data regarding which genes were present in each sequence may be communicated to the gene presence-absence matrix module 208. The gene presence-absence matrix module 208 may receive this information via any suitable wireless or hardwired connection, and generate a matrix that represents the genes present in each sample.

FIG. 6, for example, illustrates a gene presence-absence matrix 600 in accordance with one embodiment. The matrix 600 is a comprehensive observation of all the gene content of the isolate cohort (e.g., a value of "1" may indicate the particular gene is present, and a value of "0" may indicate the gene is not present). The genes' presence may also be expressed as a percentage. With this data, causal implications of the present genes for different observed phenotypes (e.g., resistance to antibiotics) of the isolates can be judged. More specifically, matrix 600 shows the reference genes and the deNovo genes from different isolates. Accordingly, genes that are common across the samples or unique to each sample can be read directly from the matrix 600.

The isolates' susceptibility to an antibiotic can be measured using the Microscan Minimum Inhibitory Concentrations (MICs)/Epsilometer (E) which may output a continuous numeric value representing an isolate's susceptibility. Labels such as sensitive or resistant may be assigned to each isolate by, for example, the microbiology or a similar division in the healthcare institution. The division assigning these labels may set a threshold level to the above mentioned numeric value that represents the isolate's susceptibility.

Once the matrix 600 is generated by the gene presence-absence matrix module 208, the gene resistance association engine 210 may identify which genes from the matrix 600 can explain the assigned labels based on a set 216 of clinical antibiotic resistance profiles of isolates. In other words, the gene resistance association engine 210 may determine which genes are responsible for or at least contribute to antibiotic resistance.

To accomplish this, in at least one embodiment the gene resistance association engine 210 may rely on statistical tests of association. According to this technique, the frequency of the presence and absence of every gene is calculated across two groups: (1) sensitive isolates; and (2) resistant isolates. This frequency can be shown on a 2×2 contingency table such as Table 1 below.

TABLE 1

Gene Frequency Contingency Table

|  | Resistant | Sensitive |
| --- | --- | --- |
| Gene Present | x | y |
| Gene Absent | a | b |

Table 1 may present the number of resistant isolates that include a particular gene (x), the number of sensitive isolates that include the particular gene (y), the number of resistant isolates that do not include the gene (a), and the number of sensitive isolates that do not include the gene (b). Any suitable univariate statistical test including the chi-squared statistical hypothesis test can be applied on the contingency table to generate a p-value representing the association of a gene with either the sensitive or resistant isolates.

The gene resistance association engine 210 may rank particular genes by their p-value (which may be corrected after multiple hypothesis testing such as Bonferroni corrections). The assigned p-values may sort the genes by their importance in explaining the susceptibility phenotype differences amongst the isolates.

Multiple genes with significant p-values could be identified by the chi-square test. Each of these genes could either operate individually or as part of a larger network of genes wherein the genes need not have large p-values. This analysis may be carried out to identify if an identified gene association is part of a larger gene operon network. This may subsequently lead to the likelihood of the operon network being a mobile genetic element/mobile gene cassette that can carry antibiotic resistance genes and move around the genome.

In other embodiments, the gene resistance association engine 210 may rely on machine learning techniques to identify which genes are responsible for or at least contribute to an isolate's resistance to antibiotics. FIG. 7 presents a table 700 of features (gene presence/gene absence) for each isolate. The number of rows n may be based on the number of observations/isolates, and the number of columns m may be based on the number of features/genes detected over all isolates. Table 700 also includes predictor labels A and B, which may represent labels of "resistant" and "sensitive", respectively, with regards to a particular antibiotic.

For example, the last isolate $S_n$ includes $gene_2$, and is labeled as sensitive to a particular antibiotic.

To process the gathered data, the gene resistance association engine 210 may use a variety of machine learning algorithms such as, but not limited to, random forest, support vector machines, back propagation neural networks, logistic regression, or the like. The algorithm used may train a mathematical model on the data, expressed in the format "y (labels)=f(features or genes)." However, the specific mathematical function may vary and may be based on the particular machine learning algorithm. The above list of machine learning algorithms is non-exhaustive and other machine learning procedures whether available now or invented hereafter may be used to accomplish the various features described herein.

For example, certain machine learning algorithms such as random forest, logistic regression, and support vector machines may predict phenotypes. These models may be trained on a training data set and can be used to predict the labels for any test isolate. The model may be validated by a k fold cross validation or random subsampling approach to determine statistics such as the true positive rate, false positive rate, area under the curve, etc.

Regardless of the machine learning model used, the model may internally assign the importance of each gene in deciding the label of an isolate. Genes with a "higher importance" value are deemed to explain the observed phenotype and are ranked higher than other genes.

Figure 8:
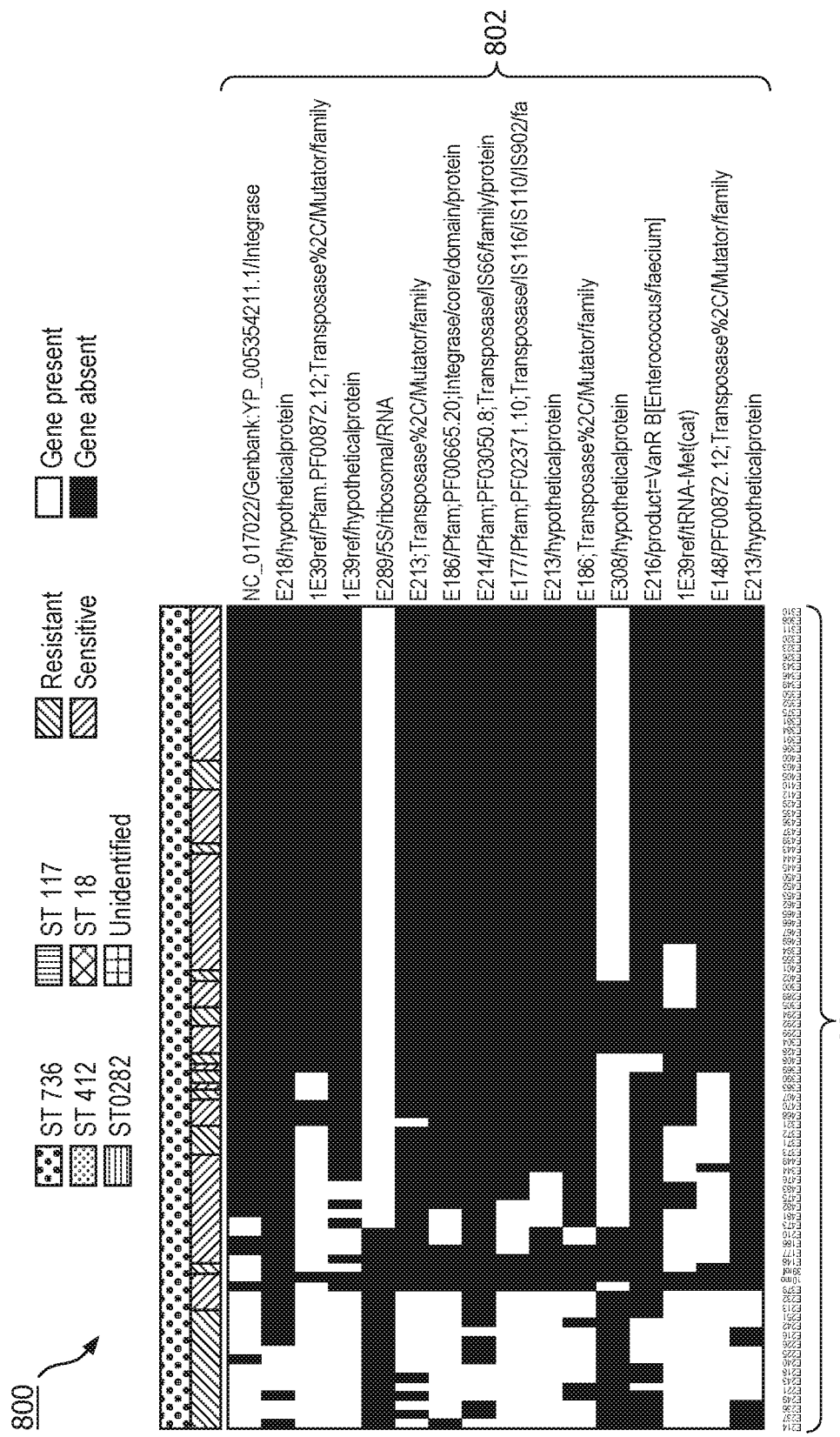
FIG. 8 depicts a gene presence-absence matrix in accordance with another embodiment.

FIG. 8 illustrates an exemplary gene presence-absence matrix 800 outputted by the gene resistance module 102. In this particular embodiment, the gene resistance module 102 was tested on 90 ST 736 *Enterococcus faecium* isolates wherein 63 were daptomycin sensitive and 27 were daptomycin resistant.

The isolates were assembled using a genome assembler and QC metrics were evaluated using QUAST (available at bioinf.spbau.ru/quast). The reference genome was a fully finished long read assembled ST 736 strain of *E. faecium* genome. The gene presence-absence matrix dimensions were 4496×90. A chi-square test on the matrix yielded 16 resistance associated genes with a p-value range between [0.000989, 0.000127]. The gene presence absence matrix 800 is shown in FIG. 8 with the genes arranged in the ascending order of their chi-square p-values 802 on the Y-axis and the isolate identification 804 on the X-axis.

Figure 9:
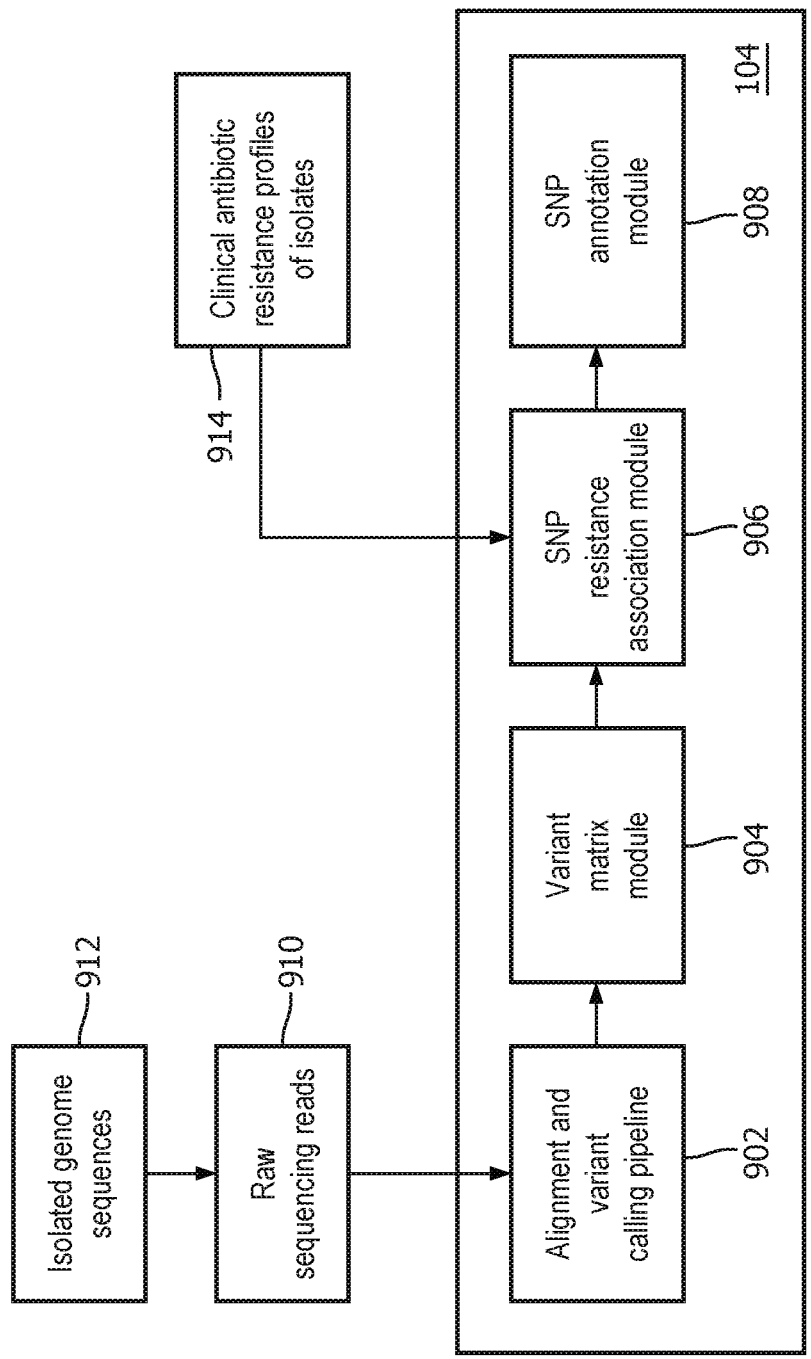
FIG. 9 illustrates the single nucleotide polymorphism (SAR) module 104 of FIG. 1 in accordance with one embodiment.

FIG. 9 illustrates the SAR module 104 in more detail. As shown, the SAR module 104 may include an alignment and variant calling pipeline module 902, a variant matrix module 904, a single-nucleotide polymorphism (SNP) resistance association module 906, and an SNP annotation module 908. The SAR module 104 may call variants on the samples with respect to a reference genome and spot variants enriched amongst the resistant samples when compared to sensitive pathogens to identify single-nucleotide polymorphisms associated with resistance.

In operation, pathogenic isolates may be extracted from patients in healthcare institutions using any suitable sequencing machine. The extracted isolates may then be cultured using any appropriate growth media such as chemically defined, complex, reducing, differential, and enrichment-based growth media. The growth media used may vary and may depend on the application. Next, DNA may be extracted from the cultured isolates using standard laboratory procedures. The extracted DNA may then be prepped for sequencing using any suitable sequencing technique such as, but limited to, HiSeq, MiSeq, PacBio, and ONP.

The raw sequences 910 of the extracted isolated genome sequences 912 may then be fed into the alignment and variant calling pipeline module 902. The alignment and variant calling pipeline module 902 may assemble the reads using alignment-based variant calling using any suitable technique. This process can either be whole genome sequencing or targeted sequencing of the pathogen's genome.

The pipeline module 902 may process the reads and compare them to one or more reference sequences. The reference sequence(s) chosen may be based on prior knowledge and/or multilocus sequence typing. The pipeline module 902 may then align the reads to the reference sequence(s) to determine where a test sequence differs from the reference sequence to call variants. The pipeline module 902 may rely on a variety of techniques and tools such as SAMTOOLS and/or GATK.

The variant matrix module 904 may then generate a variant matrix that is a comprehensive observation of all identified SNPs of the isolate cohort. FIG. 10, for example, illustrates an exemplary variant matrix 1000 in accordance with one embodiment. Matrix 1000 includes a SNP column 1002 that lists identified polymorphisms and a position column 1004 listing the positions of the SNPs in their respective genomes 1006. Column 1008 lists the nucleotides in the reference sequence at the respective positions shown in column 1004.

For example, $SNP_2$ is a detected mutation that occurs in samples $S_1$, $S_2$, and $S_3$ at position 5105. In these samples, the nucleotide at position 5105 in these sequences is guanine G, wherein the nucleotide at position 5105 in the reference sequence is adenine A.

FIG. 11 illustrates another variant matrix 1100. Similar to the table 700 of FIG. 7, however, matrix 1100 may include a column 1102 that includes either "resistant" or "sensitive" labels with respect to a particular antibiotic. With this data, causal implications of the mutations for antibiotic resistance can be determined. The isolates' susceptibility to an antibiotic can be measured using the Microscan Minimum Inhibitory Concentrations (MICs)/Epsilometer (E) which may output a continuous numeric value representing an isolate's susceptibility. The labels of resistant or sensitive may be assigned based on the numeric values exceeding a threshold level, for example.

The next step is for the SNP resistance association module 906 to identify which mutations from amongst all mutations in matrices 1000 and 1100 can explain the assigned labels based on a set 916 of clinical antibiotic resistance profiles of isolates (914). In other words, the SNP resistance association module 906 may determine which mutations are responsible for or at least contribute to antibiotic resistance.

To accomplish this, in at least one embodiment the SNP resistance association module 906 may rely on statistical tests of association. The major and minor allele counts may be calculated from the variants for each of the identified SNPs. The SNP resistance module 906 may then learn how the major and minor alleles are distributed across resistant and sensitive strains. This distribution frequency can be shown on a generated 2×2 contingency table for allele frequencies across the strains, such as Table 2 below.

TABLE 2

Allele Count Contingency table

|  | Resistant | Sensitive |
|---|---|---|
| Major Allele | x | y |
| Minor Allele | a | B |

Similar to Table 1, Table 2 forms the basis to run many univariate statistical tests including the chi-squared statistical hypothesis test. As with Table 1, the extent of the association may be represented by a generated p-value. That is, the lower the p-value, the higher the association between the SNP and drug susceptibility. That is, the presence of the SNP is a factor in whether the pathogen is resistant or sensitive to a particular antibiotic. The SNP resistance association module 906 may accordingly rank particular non-synonymous mutations according to their p-value (which may be corrected after multiple hypothesis testing such as Bonferroni corrections). The assigned p-values may sort the mutations by their importance in explaining the phenotypic differences amongst the isolates.

In other embodiments, the SNP resistance association module 906 may rely on machine learning techniques to identify which non-synonymous mutations are responsible for or at least contribute to an isolate's antibiotic resistance. These techniques may analyze data from the matrix 1000 or 1100 which, as discussed above, presents the isolates and the alleles at different variant call positions. For each variant call position, the major and minor allele can be determined.

Data presented in the matrix 1000 may be provided to the machine learning algorithm for processing. The SNP resistance association module 906 may use a variety machine learning algorithms such as, but not limited to, random forest, support vector machines, back propagation neural networks, logistic regression, or the like. This algorithm can train a mathematical model on the data, also expressed in the format "y (labels)=f(features or genes)." However, the specific mathematical function may vary and may be based on the particular machine learning algorithm or process used.

Regardless of the machine learning algorithm(s) used, the models may be validated by a k-fold cross validation or random subsampling approach to determine statistics such as the true positive rate, false positive rate, area under the generated curve, etc. The above list of machine learning algorithms and validation approaches are non-exhaustive and other techniques whether available now or invented hereafter may be used to accomplish the various features described herein.

The SNP annotation module 908 may then annotate the identified SNPs and analyze their downstream impact. For example, the SNP annotation module 908 may internally assign the importance of each SNP in deciding the label of an isolate. Accordingly, the SNPs with higher importance ratings are deemed to explain the observed phenotype (e.g., antibiotic resistance) to a greater extent than SNPs with lower importance ratings.

The SNP annotation module 908 may locate the SNP on the isolate's genome and see if it is present in a gene using any appropriate methodology. If the SNP is present in a gene, the SNP annotation module 808 may then determine whether the mutation is synonymous or non-synonymous by comparing the original codon and the SNP codon. If, on the other hand, the mutation is not present in a gene, then any biological impact may be via an e-QTL effect.

Figure 12:
FIG. 12 depicts an exemplary SNP-to-gene-mapping matrix in accordance with one embodiment.

FIG. 12 depicts an exemplary SNP-to-gene-mapping matrix 1200 in accordance with one embodiment. In this exemplary application, the SAR module 104 was tested on 104 ST 736 isolates with 68 sensitive isolates and 36 resistant isolates. 1730 combined SNP variant positions were identified amongst the 104 ST746 isolates with respect to the E39 reference genome of *E. faecium*. 717 SNPs were found to be non-synonymous mutations with 18 resistance-associated non-synonymous mutations having a chi-square p-value less than 0.05, and in the range [0.004245, 0.036]. Accordingly, the genes containing these non-synonymous mutations were deemed to be biologically meaningful in the context of antibiotic resistance.

Figures 13, 14:
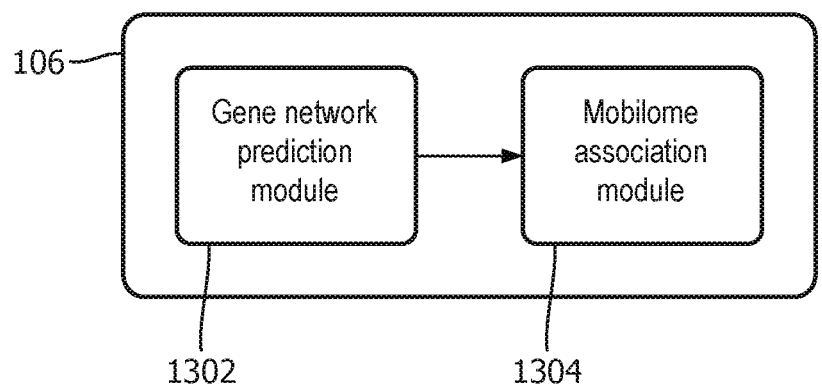
FIG. 13 illustrates the antibiotic resistance module 106 of FIG. 1 in accordance with one embodiment.
FIG. 14 depicts a combined feature matrix of genes and mutations in accordance with one embodiment.

FIG. 13 illustrates the antibiotic resistance module 106 in more detail. In this particular embodiment, the antibiotic resistance module may include a gene network prediction module 1302 and a mobilome association module 1304. The antibiotic resistance module 106 may act as a master module that integrates key biological marker information about drug susceptibility associated genes and SNPs to provide a comprehensive view on the effect of the presence and/or absence of genes and non-synonymous mutations.

The antibiotic resistance module 106 may also characterize the source of the genomic region of interest as either chromosomal or exogenously acquired DNA based on, e.g., sequence composition and/or phylogeny. Exogenously acquired DNA are mobile genetic elements that may include transposons, integrated plasmids, prophages, integrons, and insertion sequence elements. Accordingly, the antibiotic resistance module 106 is a key component in helping medical personnel such as clinicians understand the source of acquisition of resistance-causing mechanisms in hospital enriched pathogens.

The genes identified in the gene resistance module 102 and the mutations identified in the SAR module 104 can be communicated to the gene network prediction module 1302. The gene network prediction module 1302 may identify gene networks that potentially function together transcriptionally, have complementary biological functions, and have high physical proximity.

The predictions from the gene network prediction module 1302 may be communicated to the mobilome association module 1304. For example, it may be likely that the resistance phenotype is caused by a network of genes (some which may contain non-synonymous mutations) that function together and not by mutations in a single gene or by the presence/absence of an individual gene. The mobilome association module 1304 may, for example, classify operon regions as exogenous or not, which gives insight into the route of the acquisition or source of the genome elements. Information regarding the source/route of an acquired genomic element may be useful in treating and preventing antibiotic resistance.

This analysis may provide information regarding the likelihood of the operon network being part of a mobile genetic element (transposons, integrated plasmids, integrons, prophages, resistance cassettes, Insertion Sequence elements, etc.) or a genomic island that can carry antibiotic resistance genes from genome to genome.

Yet another functionality of the antibiotic resistance module 106 is to recognize the importance of genes and mutations from the gene resistance module 102 and the SAR module 104, respectively. This provides a comparison of how the genes and the SNPs contribute relatively in explaining the drug susceptibility of the isolates.

For example, FIG. 14 depicts a combined feature matrix 1400 that may be generated by the antibiotic resistance module 106. The combined feature matrix 1400 may present information regarding the most important genes and SNPs. Both genes and SNPs can be combined as features to train a machine learning model on the isolates. As shown in FIG. 14, the matrix 1400 presents genes and SNPs as binary values, wherein the major allele is assigned a "1" value and the minor allele is assigned a "0" value. Values may also be presented as a percentage, for example.

Feature selection based on the combined feature matrix 1400 may extract the genes and variants that are most responsible for or at least contribute to the variance in the observed phenotype. Accordingly, medical personnel or other interested parties may be able to identify a linear network of causal factors that explain resistance characteristics.

The antibiotic resistance module 106 may additionally or alternatively provide information on the source of acquisition of these genetic elements. For example, the antibiotic resistance module 106 may determine whether genetic elements are not part of the genome itself, but are instead acquired from the environment and are "floating genomes." As another example, the antibiotic resistance module 106 may identify whether biomarkers are part of operon networks integrated into mobile genetic elements. In other words, genes identified by the gene resistance module 102 and the non-synonymous mutations identified by the SAR module 104 can be used to identify gene networks that potentially function together transcriptionally, have complementary biological functions and have high physical proximity.

Figure 15:
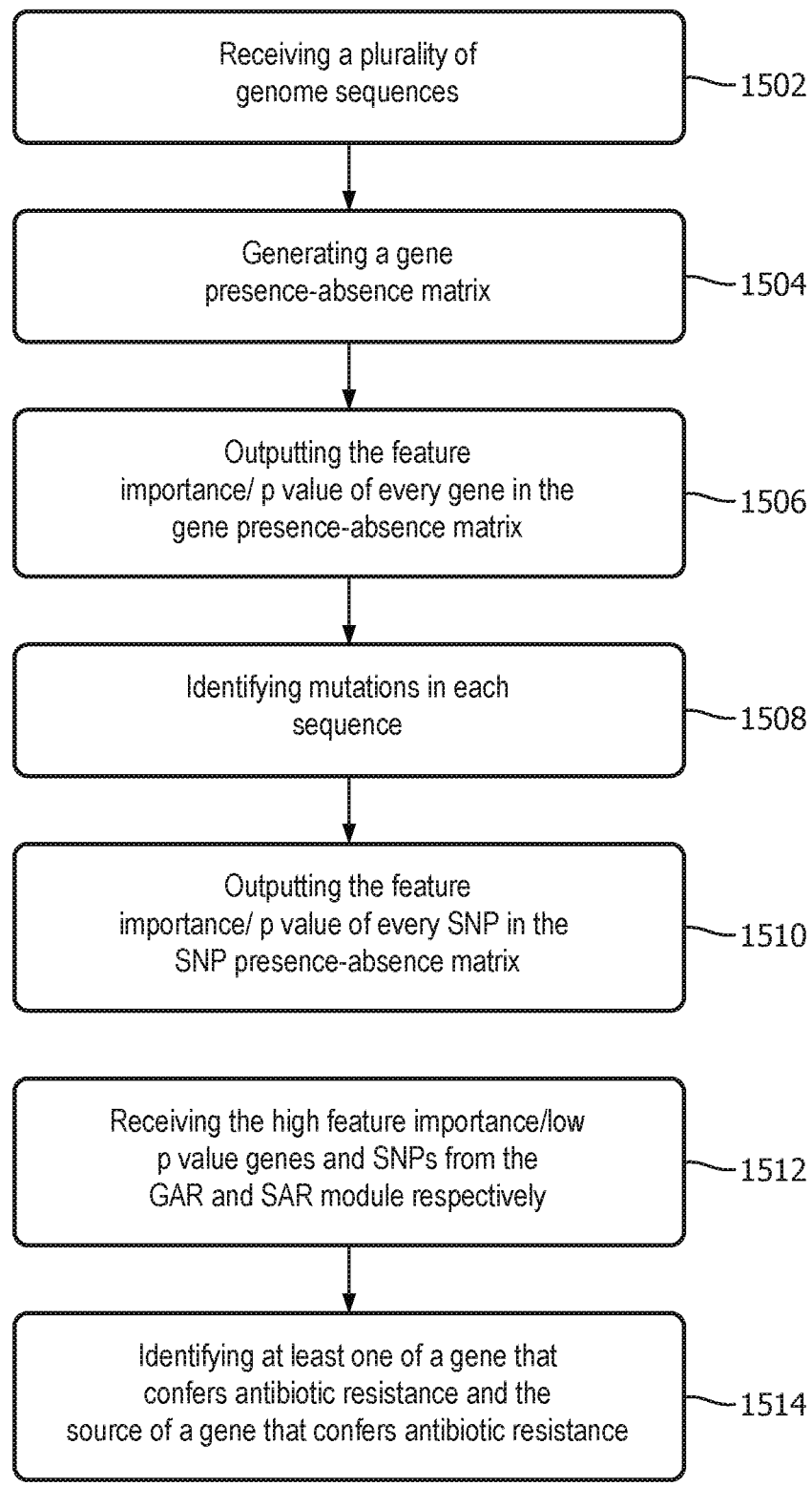
FIG. 15 depicts a flowchart of a method for identifying antibiotic resistance in pathogens in accordance with one embodiment.

FIG. 15 depicts a flowchart of a method 1500 for identifying antibiotic resistance in pathogens in accordance with one embodiment. Step 1502 involves receiving a plurality of genome sequences. These genome sequences may be received by a gene-resistance (GAR) module and a single nucleotide polymorphism (SAR) module such as those shown in FIG. 1.

Step 1504 involves generating a gene presence-absence matrix. Examples of a gene presence-absence matrix are illustrated in FIGS. 6-8. The matrix may be generated by performing the gene prediction and elimination algorithm shown in FIGS. 3-5 to identify which genes are present in each isolate sequence.

Step 1506 involves outputting the feature importance/p value for genes, which is the gene's ability to affect drug susceptibility. Accordingly, the gene presence-absence matrix generated by the gene-resistance module 102 includes a plurality of isolate sequences, the genes present in each sequence, and an identification of the sequence as resistant or sensitive (with respect to antibiotics, extracted from microbiology information).

Step 1508 involves identifying gene mutations in each of the plurality of genome sequences. These mutations may be identified by the SAR module 104 as discussed previously.

Step 1510 involves outputting the feature importance/p value for the mutations, which is the mutation's ability to affect drug susceptibility. The SAR module 104 may output a variant matrix that identifies each mutation as well as a label of resistant or sensitive (with respect to antibiotics). Accordingly, the variant matrix outputted by the SAR module 104 may include a list of isolates with mutations, the locations of said mutations, and a feature importance/p value metric corresponding to each mutation.

Step 1512 involves receiving high feature importance/low p value genes and SNPs from the GAR and SAR module respectively.

Step 1514 involves identifying at least one of a gene that confers antibiotic resistance and the source of a gene that confers antibiotic resistance based on the received labels. For example, the various components of the system 100 may analyze the identified genes, mutations, and resistant/sensitive labels using any of a plurality of machine learning tools to identify which genes/mutations are responsible for or at least contribute to antibiotic resistance. Similarly, the source of said genes/mutations that contribute to antibiotic resistance may also be determined.

Figure 16:
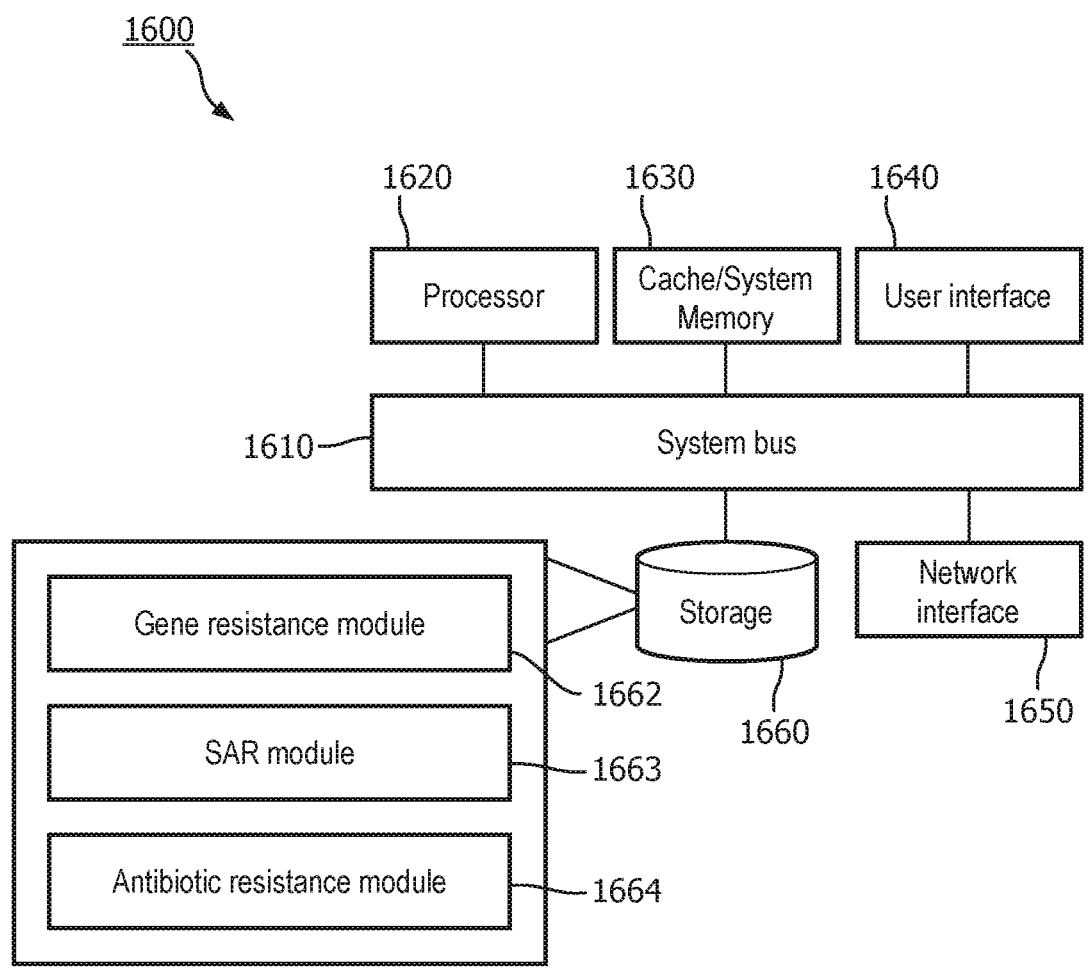
FIG. 16 illustrates an example of a hardware device for implementing the systems and methods described herein in accordance with one embodiment.

FIG. 16 illustrates an exemplary hardware device 1600 for performing the functions described herein. As shown, the device 1600 includes a processor 1620, memory 1630, user interface 1640, network interface 1650, and storage 1660 interconnected via one or more system buses 1610. It will be understood that FIG. 16 constitutes, in some respects, an abstraction and that the actual organization of the components of the device 1600 may be more complex than illustrated.

The processor 1620 may be any hardware device capable of executing instructions stored in memory 1630 or storage 1660 or otherwise capable of processing data. As such, the processor may include a microprocessor, field programmable gate array (FPGA), application-specific integrated circuit (ASIC), or other similar devices.

The memory 1630 may include various memories such as, for example L1, L2, or L3 cache or system memory. As such, the memory 1630 may include static random access memory (SRAM), dynamic RAM (DRAM), flash memory, read only memory (ROM), or other similar memory devices.

The user interface 1640 may include one or more devices for enabling communication with a user. For example, the user interface 1640 may include a display, a mouse, and a keyboard for receiving user commands. In some embodiments, the user interface 1640 may include a command line interface or graphical user interface that may be presented to a remote terminal via the network interface 1650.

The network interface 1650 may include one or more devices for enabling communication with other hardware devices. For example, the network interface 1650 may include a network interface card (NIC) configured to communicate according to the Ethernet protocol. Additionally, the network interface 1650 may implement a TCP/IP stack for communication according to the TCP/IP protocols. Various alternative or additional hardware or configurations for the network interface 1650 will be apparent.

The storage 1660 may include one or more machine-readable storage media such as read-only memory (ROM), random-access memory (RAM), magnetic disk storage media, optical storage media, flash-memory devices, or similar storage media. In various embodiments, the storage 1660 may store instructions for execution by the processor 1620 or data upon with the processor 1620 may operate.

For example the storage 1660 may include the operating system 1661 that includes a gene resistance module 1662 for identifying genes present in pathogens, a SAR module 1663 for identifying mutations present in pathogens, and an antibiotic resistance module 1664 for identifying genes and mutations that are responsible for or at least contribute to a pathogen's antibiotic resistance. The antibiotic resistance module 1664 may also determine the source of the genes or mutations that are responsible for a pathogen's antibiotic resistance.

It will be apparent that various information described as stored in the storage 1660 may be additionally or alternatively stored in the memory 1630. In this respect, the memory 1630 may also be considered to constitute a "storage device" and the storage 1660 may be considered a "memory." Various other arrangements will be apparent. Further, the memory 1630 and storage 1660 may both be considered to be "non-transitory machine-readable media." As used herein, the term "non-transitory" will be understood to exclude transitory signals but to include all forms of storage, including both volatile and non-volatile memories.

While the device 1600 is shown as including one of each described component, the various components may be duplicated in various embodiments. For example, the processor 1620 may include multiple microprocessors that are configured to independently execute the methods described herein or are configured to perform steps or subroutines of the methods described herein such that the multiple processors cooperate to achieve the functionality described herein. Further, where the device 1600 is implemented in a cloud computing system, the various hardware components may belong to separate physical systems. For example, the processor 1620 may include a first processor in a first server and a second processor in a second server It should be apparent from the foregoing description that various example embodiments may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles described herein. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention.

What is claimed is:

1. A method for identifying one or more genes that confer antibiotic resistance, the method comprising:

obtaining a reference genome sequence;

obtaining a plurality of genome sequences, each of the plurality of genome sequences comprising a plurality of genes and sequenced from a potentially pathogenic isolate obtained from a patient;

identifying, using the reference genome sequence, a set of genes present in a sample of the plurality of genome sequences;

generating in memory, by removing the identified set of genes from each of the plurality of genome sequences containing the identified set of genes, a genome sequence without the identified set of genes, wherein the steps of identifying a set of genes and generating a genome sequence without the identified set of genes are iterated at least once to generate data regarding which genes are present in each of the plurality of genome sequences;

receiving the data regarding which genes are present in each of the plurality of genome sequences;

generating in memory a gene presence-absence matrix that lists the genes present in each of the plurality of genome sequences, the presence-absence matrix comprising an identification of each of the plurality of genes within either a first column or a first row of the matrix and an identification of each of the plurality of genome sequences within the other of the either the first column or the first row, and comprising an identification, in either a row or column, of whether each of the genome sequences is obtained from an organism resistant to at least one antibiotic, and further comprising, in each intersecting cell of the presence-absence matrix, an identification of either presence of the respective gene or absence of the gene within the respective genome sequence; and determining which of the plurality of genome sequences confer antibiotic resistance;

determining which mutations in the plurality of genome sequences confer antibiotic resistance;

identifying at least one gene in the plurality of genome sequences that is associated with antibiotic resistance based on which samples and mutations confer antibiotic resistance; and reporting, via a user interface, an identification of the at least one gene or mutation that is associated with antibiotic resistance for each of the plurality of genome sequences.

* * * * *